United States Patent [19]
Gay

[11] Patent Number: 5,373,025
[45] Date of Patent: * Dec. 13, 1994

[54] SANITIZER FOR SWIMMING POOLS, SPAS, AND HOT TUBS

[75] Inventor: Walter A. Gay, Cheshire, Conn.

[73] Assignee: Olin Corporation, Stamford, Conn.

[ * ] Notice: The portion of the term of this patent subsequent to Nov. 2, 2010 has been disclaimed.

[21] Appl. No.: 75,446

[22] Filed: Jun. 14, 1993

Related U.S. Application Data

[63] Continuation-in-part of Ser. No. 840,411, Feb. 24, 1992, Pat. No. 5,258,409.

[51] Int. Cl.$^5$ .................. C07C 211/63; C07C 211/64; A01N 33/12; A61K 31/14
[52] U.S. Cl. ..................... 514/642; 504/158; 514/643; 564/281; 564/282; 564/288; 564/291
[58] Field of Search ........................ 514/642; 564/291; 504/158

[56] References Cited

U.S. PATENT DOCUMENTS

| | | | |
|---|---|---|---|
| 3,567,729 | 3/1971 | Lewis et al. | 260/268 |
| 3,624,082 | 11/1971 | Lewis et al. | 210/247.7 A |
| 3,702,298 | 11/1972 | Zsoidos et al. | 210/62 |
| 3,730,702 | 5/1973 | Shay et al. | 71/67 |
| 3,733,420 | 5/1973 | Wakeman et al. | 424/329 |
| 3,819,656 | 6/1974 | Barie, Jr. et al. | 260/343.7 |
| 4,098,602 | 7/1978 | Seymour et al. | 71/67 |
| 4,569,800 | 2/1986 | Stanley et al. | 260/501.15 |
| 4,746,368 | 5/1988 | Frank et al. | 127/525 |
| 4,806,520 | 2/1989 | Frank et al. | 502/402 |
| 4,923,619 | 5/1990 | Legros | 210/764 |
| 4,952,398 | 8/1990 | Tapin | 71/67 |
| 5,080,830 | 1/1992 | Damaso | 252/547 |
| 5,131,938 | 7/1992 | Girvan | 71/67 |
| 5,149,354 | 9/1992 | Delaney | 71/67 |

FOREIGN PATENT DOCUMENTS 59978 6/1984 European Pat. Off. .
286453A2 10/1988 European Pat. Off. .
2194227 3/1988 United Kingdom .

OTHER PUBLICATIONS

Hueck et al. "Bacteriostatic, Fungistatic and Algistatic Activity of Fatty Nitrogen Compounds", Applied Microbiology (1966) vol. 1, No. 3 pp. 308–319.
G. R. Bhat et al., "The Green Hair Problem: A Preliminary Investigation" J. Soc. Cosmet. Chem. 30 (Jan.-/Feb. 1979) (C.A. 90(20):156982r).
Landeen et al., "Efficacy of Copper and Silver Ions and Reduced Levels of Free Chlorine in Inactivation of Legionella pneumophila"; Applied & Environmental Microbiology, vol. 50, No. 12, Dec., 1989, pp. 3045–3050.
Yahya et al., "Disinfection of Bacteria in Water Systems by Using Electrolytically Generated Copper:Silver & Reduced Levels of Free Chlorine", Can. J. Microbiol. vol. 36, pp. 109–116 (1990).
George P. Fitzgerald, "Compatibility of Swimming Pool Algicides and Bactericides", Water & Sewage Works, vol. 115(2), pp. 65–71 (1968).
Federal Register vol. 56, #168, pp. 42,685–42,687, Aug. 29, 1991.
AKZO Product Bulletin for ARQUAD HTL8 (1990).
EPA Registration 5182222 information Feb. 20, 1974.
EPA Registration 5182382 information Feb. 8, 1990.

*Primary Examiner*—Peter O'Sullivan
*Attorney, Agent, or Firm*—William A. Simons

[57] ABSTRACT

A sanitizer composition comprising a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; and (b) a copper (II) ion source.

20 Claims, No Drawings

SANITIZER FOR SWIMMING POOLS, SPAS, AND HOT TUBS

CROSS-REFERENCE TO RELATED APPLICATIONS

This application is a continuation-in-part application of U.S. patent application Ser. No. 07/840,411, filed on Feb. 24, 1992 with Walter A. Gay as the named inventor now U.S. Pat. No 5,258,409, issued Nov. 2, 1993. That parent patent application is incorporated herein by reference in its entirety.

BACKGROUND OF THE INVENTION

1. Field of the Invention

The present invention relates to a sanitizer composition comprising the combination of a selected quaternary ammonium salt and a copper (II) ion source. More particularly, the present invention is directed to a sanitizer composition comprising a combination of (a) a quaternary ammonium compound selected from the group consisting of (hydrogenated tallow) 2-ethylhexyl dimethyl ammonium salt, dicoco dimethyl ammonium salt, and mixtures thereof and (b) a copper (II) ion source. Furthermore, the invention also relates to a process of sanitizing water in pools, spas and hot tubs wherein the level of bacteria in said water is lowered by treating said water with a bactericidal effective amount of this combination of selected quaternary ammonium compound and copper (II) ion.

2. Brief Description of the Prior Art

Water in swimming pools, spas and hot tubs is constantly recirculated and fresh water is normally added only to maintain the desired volume. Although this water is usually filtered continuously to keep it free of suspended matter, it frequently contains bacteria. Treatment with one or more sanitizers to control the bacteria count is necessary.

Numerous chemical compounds have been reported for use in swimming pools, spas, and hot tubs. These chemicals include various quaternary ammonium salts, copper salts, and oxidants such as chlorine sources or peroxy compounds such as hydrogen peroxide and potassium monopersulfate (OXONE). The use of combinations of such compounds is also known.

At the present time, the main disinfectant used in swimming pools, spas and hot tubs is chlorine. It is an effective bactericide, but suffers from two main disadvantages. One, it may cause eye irritation. Two, it has to be added at frequent intervals to maintain an effective concentration for killing bacteria.

Ozone has also been used as a disinfectant for swimming pools, spas and hot tubs. But, it also requires frequent or continuous dosing to maintain an effective concentration for killing bacteria. Also, if people come into contact with water containing high concentrations of ozone, such as where the ozone is injected into the water, they may experience unpleasant headaches and the like.

Quaternary ammonium compounds have also been reported as being useful in swimming pools, spas, and hot tubs as bacteristats, bactericides, or algaecides. Those used as bacteristats and bactericides have required relatively high levels (e.g. over 100 ppm by weight) to be effective or have required prolonged contact-times. However, at such high concentration levels, quaternary ammonium salts in general have the potential of producing objectionable, aesthetically unpleasing turbid swimming pool water having a high total organic carbon (TOC) content. Furthermore, such high concentrations of quaternary ammonium salts may increase the likelihood of skin irritation of people using those bathing facilities.

Quaternary ammonium salts have also been used in swimming pools, spas and hot tubs as algaecides. For example, known commercial algaecide products include SUN ® Algae Prevention (an alkyl dimethyl benzyl ammonium chloride) and HTH ® Non-Foaming Algaecide Concentrate [poly[oxyethylene-(dimethyliminio)ethylene(dimethyliminio) ethylene dichloride]]. Such algaecides are used in relatively low concentrations (under 10 ppm by weight). At such concentrations, these known quaternary ammonium algaecides do not act as effective bactericides.

In practice, harmful bacteria must be killed rapidly if they are present in a swimming pool, spa or hot tub. Indeed, the standard test method for disinfectants in swimming pools [American Organization of Analytical Chemists (A.O.A.C.) test method 4.047 entitled "Disinfectants (Water) for Swimming Pools"] requires that a swimming pool bactericide kills high levels of bacteria in only 30 seconds of contact. With quaternary ammonium salts, this rapid bactericidal activity must be accomplished at low concentrations, e.g., 60 ppm or less, to avoid the potential of producing objectional, unpleasing turbid swimming pool water having a high total organic carbon (TOC) content as well as increasing the likelihood of skin irritation of people using these bathing facilities.

It is believed that the present invention represents a viable alternative to the above-noted problems with existing swimming pool, spa and hot tub bactericides.

Examples of references describing the use of individual quaternary ammonium compounds or other water-treatment bactericides or combinations of bactericides for water-treatment and other applications include:

U.S. Pat. No. 3,510,424, which issued to Zumbrunn on May 5, 1970, teaches that inorganic and organic peroxoacids such as peroxosulfuric acid and its salts and peroxodisulfuric acid and its salts may be used to convert toxic cyanides in industrial effluent streams to nontoxic and hydrolysable cyanates.

U.S. Pat. No. 3,567,729, which issued to Lewis et al. on Mar. 2, 1971, teaches the use of certain quaternary ammonium salts as germicides.

U.S. Pat. No. 3,624,082, which issued to Lewis et al. on Nov. 30, 1971, teaches a process for making selected quaternary ammonium salts which may be useful as germicides.

U.S. Pat. No. 3,702,298, which issued to Zsoidos et al. on Nov. 7, 1972, teaches a method of treating swimming pools with a combination of a peroxy salt, such as salts of peroxymonosulfuric acid, and a copper salt.

U.S. Pat. No. 3,730,702, which issued to Shay et al. on May 1, 1973, teaches a method of inhibiting microorganisms by applying thereto selected water-soluble unsymmetrical di-higher alkyl dimethyl ammonium salts. This product may be used to disinfect hard surfaces, fabrics, topical portions of the body and water.

U.S. Pat. No. 3,733,420, which issued to Wakeman et al. on May 15, 1973, teaches a method of inhibiting microorganisms in hard water aqueous solutions [e.g., swimming pools (see col. 3, line 15)] using octyl dodecyl dimethyl ammonium salts. It is noted that this invention is stated to be useful for bactericidal purposes (see col. 4, line 11).

U.S. Pat. No. 3,845,216, which issued to Brink et al. on Oct. 29, 1974, teaches a method of controlling the growth of bacteria in aqueous systems by contacting the system with a combination of B-bromo-B-nitro-styrene and didecyl dimethyl ammonium chloride.

U.S. Pat. No. 4,098,602, which issued to Seymour et al. on Jul. 4, 1978, teaches an algicidal composition comprising selected ammonium quaternary compounds and a copper complex formed by reacting a water insoluble copper compound and alkanol amines.

U.S. Pat. No. 4,311,598, which issued to Verachtert on Jan. 19, 1982, describes a process for the disinfection of a bacteria-containing aqueous medium by contacting that medium with a combination of hydrogen peroxide or peroxyacid, a soluble copper salt and an autoxidisable reducing agent (e.g., 1,2,3-trihydroxybenzene, benzaldehyde, dihydroxy fumaric acid, malonic acid, ascorbic acid, or an alkali metal sulfate.

U.S. Pat. No. 4,444,790, which issued to Green et al. on Apr. 24, 1984, teaches the use of "branched decyl" n-decyldimethyl quaternary ammonium salts as disinfectants for aqueous solutions.

U.S. Pat. No. 4,450,174, which issued to Green et al. on May 22, 1984, describes the use of di-n-decyl dimethyl quaternary ammonium salts to inhibit bacteria in aqueous systems.

U.S. Pat. No. 4,594,091, which issued to Givan on Jun. 10, 1986, is directed to the use of certain boron derivatives to inhibit algal and fungal growth in water.

U.S. Pat. No. 4,790,940, which issued to Costaldi et al. on Dec. 13, 1988, teaches a process for the treatment of free cyanide-containing wastewater to destroy the free cyanide content thereof by treating said waters under alkaline conditions with polysulfide in the presence of a cationic surfactant catalyst (e.g., dialkyl dimethyl quaternary ammonium salt).

U.S. Pat. No. 4,923,619, which issued to Legros on May 8, 1990, teaches the treatment of water of swimming pools and industrial water by means of a combination of (a) quaternary ammonium salts and (b) water-soluble copper and/or silver salts and peroxide compounds releasing oxygen, such as monopersulfate or peroxidisulfate of potassium. See col. 1 of this patent.

U.S. Pat. No. 4,952,398, which issued to Tapin on Aug. 28, 1990, teaches the treatment of swimming pool water using the combination of a quaternary ammonium compound and a copper salt as a biocide.

U.S. Pat. No. 5,131,938, which issued to Girvan on Jul. 21, 1992, suggests that certain boron derivatives may be used for killing algae and fungus in swimming pools. This patent further teaches that these boron derivatives may be used with known pool sanitizers (e.g., halogens, copper, hydrogen oxide, ozone, oxone, and quaternary ammonium compounds). See col. 5 of this patent.

U.S. Pat. No. 5,149,354, which issued to Delaney on Sep. 22, 1992, suggests a composition to inhibit the growth of algae, fungi, and bacteria, and to prevent the formation of turbidity in pool water comprising certain amounts of (a) copper sulfate, (b) silver nitrate, (c) sodium gluconate, (d) zinc chloride or zinc sulfate, (e) water, and (f) a complexone capable of forming water-soluble copper complexes (e.g., EDTA or a suitable alkali metal salt thereof).

United Kingdom Patent Application 2,194,227, filed by Crystalclear S. A. and published on Mar. 2, 1988, teaches treating a body of water, such as a swimming pool, by adding thereto a liquid component and an oxidizing component. The liquid component comprises a polymeric cationic quaternary ammonium compound, a sequestering agent, and a copper salt. The oxidizing component may include sodium perborate, potassium persulfate, an alkali or alkaline earth hypochlorite, a trichloroisocyanurate, or an alkali metal dichlorosiocyanurate.

European Patent No. 59,978, which was granted to Bayrol on Jun. 13, 1984, claims a process for the disinfection of water and the oxidative decomposition of oxidizable impurities contained in the water, by adding to the water the combination of (a) quaternary ammonium compounds, (b) water-soluble copper salts and or silver salts, and (c) an oxygen-liberating peroxide compound (e.g., potassium hydrogen monopersulfate).

European Patent Application No. 0286453, which was filed by Pernox Manufacturing Company and published on Oct. 12, 1988, describes a biocidal composition for the treatment of water comprising certain quaternary ammonium compounds together with copper cations and/or a biocide containing a gem. halonitromethylene group.

G. R. Bhat et al. "The Green Hair Problem: A Preliminary Investigation", J. Soc. Cosmet. Chem. Vol. 30, 1-8 (January/February 1979) suggests that the combination of copper and peroxide enhances the phenomenon of blond hair acquiring a green tint. The experiments ill this paper included a test where the blond hair was oxidized with hydrogen peroxide and immersed in a commercial formulation of a quaternary ammonium compound (distearyl dimethyl ammonium chloride).

L. K. Landeen et al. "Efficacy of Copper and Silver Ions and Reduced Levels of Free Chlorine in Inactivation of Legionella Pneumophila", Applied and Environmental Microbiology, Dec. 1989 pages 3045-3050, describes the activity of copper and silver ions in the presence of low levels of free chlorine against Legionella pneumophila.

M. T. Yahya "Disinfection of Bacteria in Water Systems by using Electrolytically Generated Copper:-Silver and Reduced Levels of Free chlorine", Con. J. Microbiol. Vol. 36, pages 109-116, 1990, describes the activity of copper or silver ions with low levels of free chlorine against various bacteria in water.

G. P. Fitzgerald "Compatibility of Swimming Pool Algicides and Bactericides, Water & Sewage Works, Vol. 115(2), pages 65-71 (1968), teaches that various amines, quaternary ammonium compounds, copper and silver salts have algistatic, algicidal, and bactericidal properties in swimming pools.

U.S. EPA Freedom of Information Request RIN-5973-92 shows that Bio-Guard MSA Algicide made by Bio-Lab, Inc. of Decatur, GA in 1974 contained the combination of copper and a quaternary ammonium compound (dimethyl dichlorobenzyl ammonium chloride).

Separately, (hydrogenated tallow) 2-ethylhexyl dimethyl ammonium chloride (sold commercially as ARQUAD HTL8-Cl) has been used for several uses including the following:

- AKZO Product Bulletin for ARQUAD HTL8 (copyrighted 1990) describes the product characteristics for ARQUAD HTL8-Cl and ARQUAD HTL8-MS and their uses in hair care.
- U.S. Pat. No. 4,569,800, which issued to Stanley et al. on Feb. 11, 1986, teaches that (hydrogenated tallow) 2-ethylhexyl dimethyl ammonium chloride may be used in a fabric softening solution.
- U.S. Pat. Nos. 4,746,368 and 4,806,590 which issued to Frank et al. on May 24, 1988 and February 21, 1989, respectively, suggests the use of ARQUAD-type quaternary ammonium salts to remove impurities (e.g., phenolics, amino nitrogen containing compounds, and various other color bodies) from aqueous saccharide solutions.
- U.S. Pat. No. 5,080,830, which issued to Damaso on Jan. 14, 1992, describes the use of (hydrogenated tallow) 2-ethylhexyl dimethyl ammonium chloride in a hair conditioner or hair shampoo.
- Federal Registry, Vol. 56, No. 168, Thursday, Aug. 29, 1990, states that dimethyl (2-ethylhexyl) hydrogenated tallow ammonium chloride is safe to use as a decolorizing agent in the clarification of refinery sugar liquors.

BRIEF SUMMARY OF THE INVENTION

One aspect of the present invention is directed to a sanitizer composition comprising a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; (b) a copper (II) ion source.

Another aspect of the present invention is directed to a process for sanitizing water in a swimming pool, spa or hot tub wherein the level of bacteria in said water is lowered comprising treating said water with a bactericidal effective amount of the combination of (a) a quaternary ammonium compound selected from the group consisting of a (hydrogenated tallow) 2-ethylhexyl dimethyl ammonium salt; a dicoco dimethyl ammonium salt; and mixtures thereof and (b) a copper (II) ions, the concentration of said quaternary ammonium salt being less than about 60 parts per million (ppm) by weight.

DESCRIPTION OF PREFERRED EMBODIMENTS

The two classes of quaternary ammonium salts employed in the present invention are (hydrogenated tallow) 2-ethylhexyl dimethyl ammonium salts and dicoco dimethyl ammonium salts. Mixtures of species within or between these two classes may also be employed. The anion for these salts can be any biocidally acceptable anion such as a halide, sulfate, methosulfate, acetate, borate, glucomate and the like. Chloride, bromide and methosulfate are the preferred anions.

The preferred (hydrogenated tallow) 2-ethylhexyl dimethyl ammonium salts are (hydrogenated tallow) 2-ethylhexyl dimethyl ammonium chloride and (hydrogenated tallow) 2-ethylhexyl dimethyl ammonium methosulfate. The preferred dicocodi methyl ammonium salt is dicocodi methyl ammonium chloride.

Tallow is a mixture of $C_{14}$ to $C_{18}$ hydrocarbon groups with a preponderance of saturated $C_{18}$. Hydrogenated tallow is tallow in which the number of unsaturated groups have been at least partially reduced.

The coco radical is a radical group derived from coconut fatty acids. The coco radical is a mixture of $C_8$ to $C_{18}$ hydrocarbons with a preponderance of $C_{12}$ and $C_{14}$ hydrocarbon groups in proportions approximately to the sources from which they are derived. A typical alkyl group distribution of a coco radical in dicocodi methyl ammonium chloride is octyl 6%; decyl 7%; dodecyl 46%, tetradecyl 18%; hexadecyl 11%; octadecyl 3%; and unsaturated $C_{18}$ 9%.

All three of these preferred salts are commercially available. (Hydrogenated tallow) dimethyl ammonium chloride is available as ARQUAD ® HTL8-Cl from Akzo Chemicals, Inc. of Chicago, Ill. (Hydrogenated tallow) dimethyl ammonium methosulfate is available as ARQUAD ® HTL8-MS from Akzo Chemicals, Inc. of Chicago, Ill. Dicocodimethyl ammonium chloride is available from many sources, including as ARQUAD ® 2C-75 from Akzo Chemicals, Inc. of Chicago, Ill.

The source of copper (II) ions used in the present invention may be any source of copper (II) cations including any water-soluble copper (II) salt which has a biocidally acceptable anion, which is capable of solubilizing copper (II) cations in water and is compatible with the above-noted quaternary ammonium salts.

Examples of such copper (II) salts include copper (II) carbonate, copper (II) benzoate, copper (II) bicarbonate, copper (II) nitrate, copper (II) nitrite, copper (II) chloride, copper (II) sulfate, copper (II) acetate, copper (II) formate, copper (II) trichloroacetate, copper (II) triethanolamine complex, copper (II) ethylenediamine tetraacetic acid complex, copper (II) citrate, copper (II) gluconate, and mixtures thereof. The preferred water-soluble copper (II) salt is copper (II)سulfate.

The present application recites "a bactericidal effective amount of the combination" of said quaternary ammonium salts and said copper (II) ions. This term, as used in the present specification and claims means any total amount of these two components which results in an effective bactericidal activity against at least 99.9%, preferably 99.99%, of the bacteria initially present in the water treated with said combination. In other words, if a body of water containing one million colony forming units (CFU's) of bacteria per milliliter was treated in accordance with the present invention, then less than 1,000 colony forming units (CFU's), or preferably less than 100 CFU's, will be left per milliliter after contact with this combination.

Preferably, it is also desired that the amounts of each component in this combination be sufficient to cause a rapid decrease or lowering of the bacteria within about 60 seconds from contact, more preferably within about 30 seconds, so as to meet the requirements of the above-noted standard test method for disinfectants in swimming pools (A.O.A.C. Test Method 4.047).

The preferred weight ratio of these quaternary ammonium salts to copper (II) ion source is from about 3:1 to about 600:1. With respect to the preferred (hydrogenated tallow) 2-ethylhexyl dimethyl ammonium chloride and methosulfate salts to the preferred copper (II) source, copper (II) sulfate, it is more preferred to employ a weight ratio from about 10:1 to about 150:1, most preferably about 25:1 to 75:1. With respect to the preferred dicocodimethyl ammonium chloride to the preferred copper (II) ion source, copper (II) sulfate, it is more preferred to employ a weight ratio from about 30:1 to about 300:1, most preferably, about 60:1 to 150:1.

These selected quaternary ammonium salts and copper (II) ion sources may be combined in any conventional way. Preferably, it may be desirable to simply mix them together for later addition to a swimming pool, spa or hot tub.

Other conventional water-treatment chemicals may be combined with the two above-noted critical components of the present invention. Such conventional chemicals may include defoamers, perfumes, insect repellants, flocculents, and sequestering agents.

Generally, the above-noted combination of the present invention is employed in an aqueous solution containing these two critical components and any optional components. It is desirable that these aqueous solutions would contain from about 10% to about 80% by weight solids (i.e., the components other than water). Such aqueous solutions may be directly added to swimming pools, spas, and hot tubs in bactericidal effective amounts which can be easily calculated by pool operators. The present invention also encompasses the combination of two aqueous solutions being employed together where one aqueous solution contains the above-noted quaternary ammonium salt and the second aqueous solution contains the copper (II) ion source. A combination of solid components is also encompassed by this invention.

The above-noted second aspect of the present invention is drawn to a process of sanitizing water in swimming pools, spas or hot tubs wherein the level of bacteria in said water is lowered by contacting said water with a bactericidal effective amount of the combination of these two critical components. This second aspect of the present invention is also limited to having a maximum of about 60 ppm by weight of the quaternary ammonium salt component in said water. Preferably it is preferred to use about 5 to about 40 parts per million by weight of the quaternary ammonium salt in the water of the swimming pool, spa or hot tub. This maximum limit of about 60 ppm is necessary to avoid the potential of producing objectionable, aesthetically unpleasing turbid water having a high total organic carbon (TOC) content and to decrease the likelihood of any skin irritation of bathers using these facilities.

While being limited to this maximum concentration of the quaternary ammonium salt, it is preferred that the combined concentration of the quaternary ammonium salts and copper (II) ions be high enough to cause a decrease of at least 99.9% of the bacteria in the water within 60 seconds, more preferably within 30 seconds, after contact with said combination. Accordingly, it is preferred to employ about 0.1 to about 2 ppm by weight, more preferably about 0.5 to 1 ppm by weight, of copper (II) ions in said water.

For this second aspect of the present invention, the selected quaternary ammonium salts and copper (II) ion source may be added together or separately at the same time to the water to be treated. As mentioned above, it is desirable to add an aqueous solution containing the combination of these two components, which is the first aspect of the present invention.

In the present process, a person would only want to dissolve the quaternary ammonium compound and copper (II) ions source in the water of the swimming pool, spa or hot tub being treated and ensure a uniform concentration of each in the above ranges is achieved.

Depending upon the particular aqueous medium being treated and upon various external factors, redosing of the combination of the present invention may be necessary. For example, a heavily used swimming pool may require redosing at more frequent intervals than another pool of the same size which was used only occasionally or lightly. Redosing of the quaternary ammonium salt and copper (II) ion source may be carried out together or individually. Pool operators may use standard testing kits to determine the concentration of each component and whether or not (and how much) redosing is needed.

For some water treatment applications, it may be desirable to add other water treatment chemicals such as algaecides or oxidants. Oxidants may include chlorine sources and peroxy compounds. Chlorine sources may include calcium hypochlorite, chlorinated isocyanurates, chlorinated glycolurils, chlorinated hydantoins, chlorinated imidazolidinones, chlorinated oxazolidinones, chlorinated amines and the like as well as mixtures thereof. It is expected that analogous bromine compounds could also be used as oxidants.

Peroxy compound may include hydrogen peroxide solutions as well as salts of acids selected from the group consisting of peroxydisulfuric acid, peroxymonosulfuric acid, peroxydicarbonic acid, peroxymonocarbonic acid, peroxydiphosphoric acid, peroxymonophosphoric acid, perboric acid and mixtures thereof. The preferred peroxy compounds are potassium peroxymonosulfate (also known as OXONE) and hydrogen peroxide solutions.

Generally it is desired to add these other water-treatment chemicals at intervals to effect a "shock treatment" on the body of water being treated. The desired concentration of such other water-treatment chemicals will depend upon the particular chemical employed and the specific application required.

By practice of the present invention, one is able to rapidly and economically sanitize water in swimming pools, spas and hot tubs to safe and acceptable bacteria levels. Furthermore, at the very low concentrations found to be effective, the particular quaternary ammonium compounds have no effect on the eyes, no objectionable odor or taste, and do not bleach clothing as may happen with the use of chlorine or ozone. Furthermore, this invention is believed effective against bacteria resistant to the present quaternary ammonium salts alone.

The following experiments are provided to better understand the present invention. All parts and percentages are by weight and temperatures are degrees Celcius, unless explicitly stated otherwise.

COMPARATIVE LABORATORY TESTING A.
Inoculum Preparation

E. coli, ATCC 11229, were grown on tryptic soy agar slants for 18 to 24 hours at 35° C. The slants were then washed with 10 ml of sterile saline (0.85% by weight NaCl) and centrifuged at 10,000 revolutions per minute for 10 minutes. The supernatant was discarded, and the culture resuspended in 10 ml of sterile saline (0.85%). The centrifugation and removal of supernatant steps were repeated two times. The culture was then resuspended in sterile reverse osmosis water, and the culture suspension adjusted to an optical density of 0.2 at 550 nm using a Bausch & Lomb colormeter, Model No. 20. The final culture suspension is approximately 200,000,000 viable cells per milliliter, i.e., 200,000,000 colony forming units/ml or 200,000,000 cfu/ml.

B. Preparation of Test Solutions

The test used herein as a standard to verify and demonstrate the bactericidal activity of the quaternary ammonium salts of the invention is a variation of the American Organization of Analytical Chemists (A.O.A.C.) procedure 4.047 entitled "Disinfectants (Water) for Swimming Pools". The variation, which makes the test more stringent, consists of using dechlorinated tap-water, having an alkalinity of 100 ppm and a calcium hardness of 90–100 ppm. The quaternary ammonium salt solutions were prepared at a pH of 7.5 with the concentrations given in Tables 1 and 2. A stock copper ($Cu^{+2}$) solution was prepared at 100-fold the test concentration from copper sulfate pentahydrate with the solution having a pH 5.5. A stock oxidizer solution was prepared at 100-fold the test concentration from OXONE® monopersulfate compound (potassium peroxymonosulfate) with the solution having a pH 7.5.

C. Bactericidal Efficacy Testing

The quaternary ammonium salts, copper as $Cu^{+2}$, and oxidizer as OXONE monopersulfate compound were evaluated at the concentrations set forth in Tables 1 and 2 either by themselves or in the indicated combinations. For tests involving individual components, 10 ml of the appropriate solution or sterile reverse osmosis water were added aseptically to sterile, capped culture tubes. For tests involving combinations of ingredients, 10 ml of the quaternary ammonium salt solution were added aseptically to sterile, capped culture tubes and appropriate volumes of the copper stock solution and/or the OXONE monopersulfate compound stock solution were added less than 5 minutes before the addition of the culture suspension to start the timed exposure.

To the above-described test solutions, at room temperature, 50 microliters of bacterial suspension were added, and the time of addition recorded as zero time. Immediately after adding the bacteria suspension, the reaction mixture was vortexed for 10 seconds, and 1 milliliter samples taken at times shown in Tables 1 and 2. Just prior to each sampling, the vortexing procedure was repeated. Each 1 milliliter sample was added immediately to 9 ml of a neutralizer to achieve a 1:10 dilution. The neutralizer (pH of 7.5) was made by combining (a) 33.4 milliliters of an aqueous solution containing 4% by weight azolectin and 28% by weight TWEEN ®80; (b) 8.33 milliliters of a standard phosphate buffer; and (c) 558.33 milliliters of distilled water to make a 600 milliliter stock neutralizer solution. This solution was autoclaved for 20 minutes at 121° C. to kill any organisms therein. A second stock neutralizer solution was similarly prepared for those tests in which copper (II) ions or OXONE would be present. This second neutralizer stock was prepared the same way except 0.6 grams of sodium thiosulfate and 0.6 grams of sodium thioglycolate were added to the 600 milliliter solution before autoclaving. Controls were run to insure that compounds are effectively neutralized. About 1,000,000 of the test bacteria were exposed to each test solutions.

After neutralization at the selected time-of-contact, 1 milliliter portions of the neutralized samples were added to plastic petri dishes, and tempered tryptone glucose extract agar added to each plate. The plates were then incubated at 37° C. for about 48 hours and colonies were counted. The numbers are corrected to cfu/ml by applying the appropriate dilution factor used, e.g. a count of 300 colonies per plate is 300 cfu/ml, if no dilution was used and 3,000 cfu/ml, if a 10-fold dilution was used.

TABLE 1

SYSTEMS INEFFECTIVE AS RAPID-KILL BACTERICIDES

| Quat (ppm) | $Cu^{+2}$ (ppm) | OXONE (ppm) | E.Coli Remaining (cfu/ml) | | | |
|---|---|---|---|---|---|---|
| | | | 0.5 Min. | 1.0 Min. | 3.0 Min. | 5.0 Min. |
| Didecyl dimethyl ammonium chloride | | | | | | |
| 10 | 0 | 0 | >3,000 | >3,000 | >3,000 | >3,000 |
| 10 | 0.5 | 0 | >3,000 | >3,000 | >3,000 | >3,000 |
| 10 | 0 | 12 | >3,000 | >3,000 | >3,000 | >3,000 |
| 10 | 0.5 | 12 | >3,000 | >3,000 | >3,000 | >3,000 |
| 20 | 0 | 0 | >3,000 | — | — | 5 |
| 20 | 1 | 0 | >3,000 | — | — | >3,000 |
| 20 | 0 | 12 | >3,000 | — | — | 15 |
| 20 | 1 | 12 | >3,000 | — | — | >3,000 |
| 20 | 1 | 24 | >3,000 | >3,000 | 30 | 0 |
| Di-isodecyl dimethyl ammonium chloride | | | | | | |
| 10 | 0 | 0 | >3,000 | >3,000 | >3,000 | >3,000 |
| 10 | 0.5 | 0 | >3,000 | >3,000 | >3,000 | >3,000 |
| 10 | 0 | 12 | >3,000 | >3,000 | >3,000 | >3,000 |
| 10 | 0.5 | 12 | >3,000 | >3,000 | >3,000 | >,3,000 |
| 20 | 0 | 0 | >3,000 | 1,430 | 115 | 10 |
| 20 | 0.5 | 0 | >3,000 | >3,000 | >3,000 | >3,000 |
| 20 | 0 | 12 | >3,000 | >3,000 | >3,000 | 305 |
| 20 | 0.5 | 12 | >3,000 | >3,000 | >3,000 | >3,000 |
| Stearyl trimethyl ammonium chloride | | | | | | |
| 10 | 0 | 0 | >3,000 | >3,000 | >3,000 | >3,000 |
| 10 | 0.5 | 0 | >3,000 | >3,000 | >3,000 | >3,000 |
| 10 | 0 | 12 | >3,000 | >3,000 | >3,000 | 1,110 |
| 10 | 0.5 | 12 | >3,000 | >3,000 | >3,000 | 590 |
| 20 | 1 | 24 | >3,000 | >3,000 | 1,425 | 0 |
| Octyl trimethyl ammonium chloride | | | | | | |
| 10 | 0 | 0 | >3,000 | >3,000 | >3,000 | >3,000 |
| 10 | 0.5 | 0 | >3,000 | >3,000 | >3,000 | >3,000 |
| 10 | 0 | 12 | >3,000 | >3,000 | >3,000 | >3,000 |
| 10 | 0.5 | 12 | >3,000 | >3,000 | >3,000 | >3,000 |
| 20 | 1 | 24 | >3,000 | >3,000 | >3,000 | >,3,000 |
| Dioctyl dimethyl ammonium chloride | | | | | | |
| 10 | 0 | 0 | >3,000 | >3,000 | 170 | 30 |
| 10 | 0.5 | 0 | >3,000 | >3,000 | 345 | 100 |
| 10 | 0 | 12 | >3,000 | >3,000 | 2,105 | 90 |
| 10 | 0.5 | 12 | >3,000 | >3,000 | 945 | 135 |
| 20 | 1 | 24 | >3,000 | >3,000 | 40 | 0 |
| No Quaternary Ammonium Salt | | | | | | |
| 0 | 1 | 0 | >3,000 | >3,000 | >3,000 | >3,000 |
| 0 | 0 | 24 | >3,000 | >3,000 | >3,000 | >3,000 |
| 0 | 1 | 24 | >3,000 | >3,000 | >3,000 | >3,000 |

TABLE 2

SYSTEMS EFFECTIVE AS RAPID-KILL BACTERICIDES

| Quat (ppm) | $Cu^{+2}$ (ppm) | OXONE (ppm) | E.Coli Remaining (cfu/ml) | | | |
|---|---|---|---|---|---|---|
| | | | 0.5 Min. | 1.0 Min. | 3.0 Min. | 5.0 Min. |
| (Hydrogenated tallow) 2-ethylhexyl dimethyl ammonium chloride | | | | | | |
| 10 | 0 | 0 | 40 | 30 | 10 | 5 |
| 10 | 0.5 | 0 | 35 | 10 | 15 | 5 |
| 10 | 0 | 12 | 30 | 10 | 5 | 0 |
| 10 | 0.5 | 12 | 55 | 10 | 30 | 40 |
| 20 | 0 | 0 | 30 | 30 | 5 | 5 |
| 20 | 0.5 | 0 | 10 | 5 | 0 | 15 |
| 20 | 0 | 12 | 20 | 15 | 0 | 0 |
| 20 | 0.5 | 12 | 0 | 0 | 0 | 20 |
| Repeat Test | | | | | | |
| 10 | 0 | 0 | 30 | 10 | 0 | 5 |
| 10 | 0.5 | 0 | 15 | 0 | 0 | 0 |
| 10 | 0 | 12 | 10 | 5 | 0 | 0 |
| 10 | 0.5 | 12 | 5 | 15 | 0 | 0 |
| Dicoco dimethyl ammonium chloride | | | | | | |
| 20 | 0 | 0 | 575 | — | — | 25 |
| 20 | 1 | 0 | 1,030 | — | — | 140 |
| 20 | 0 | 12 | 430 | — | — | 40 |
| 20 | 1 | 12 | 1,500 | — | — | 80 |

D. Conclusions

Table 1 shows data for testing a wide variety of dialkyldimethyl ammonium salts and alkyl-trimethyl quaternary ammonium salts at 10-20 ppm as bactericides with potentially rapid-kill, i.e., greater than 99.9% in an aqueous environment; a rapid-kill time being equal or less than about 1 minute. Copper is added since its presence at about 0.1 ppm or greater is believed to give further effectiveness in controlling bacteria resistant to the quaternary ammonium salts. The OXONE monoper-sulfate compound is a commercially available oxidizer that is added primarily to destroy undesirable organic compounds, e.g., suntan lotion, humic acids from decaying leaves in swimming pools when used at typical concentrations from 12 to 24 ppm as a shock treatment.

Test results show that in the absence of a quaternary ammonium salt, the use of either copper at 1 ppm or OXONE monopersulfate compound at 24 ppm or the combination of copper (1 ppm) with OXONE monopersulfate compound (24 ppm) failed to show acceptable bactericidal efficacy.

Dimethyl dialkyl quaternary ammonium salts are a major class of quaternary ammonium salts and several of these were tested with and without copper and/or OXONE monopersulfate compound. Didecyl dimethyl ammonium chloride by itself was ineffective at 10 ppm and was also ineffective with copper and/or OXONE monopersulfate compound at 0.5 ppm and 12 ppm, respectively. At 20 ppm, this quaternary ammonium salt was ineffective at the short contact time of 0.5 min. and required up to 5 minutes for significant bacteria-kill to result. However, even at this high concentration and long contact time, efficacy was diminished when copper was added for resistant bacteria control.

Changing of the normal-decyl groups to branched decyl groups, e.g., isodecyl groups, in the above structure gave similar poor rapid-kill bactericidal activity when tested alone and loss of activity at higher concentration of quaternary ammonium salt if copper was added.

Similar poor control of bacteria at short contact time was observed for dioctyl dimethyl ammonium chloride, with the presence of copper again serving to decrease activity further.

The trimethyl alkyl quaternary ammonium salts are another major class of quaternary ammonium salts, and these were tested with the fourth group being as low as eight carbons in length (octyl) or as high as 18 carbons in length (stearyl). As seen, neither showed acceptable rapid bacteria-kill by itself-or in the presence of copper and/or OXONE monopersulfate compound.

In light of the above results, it was thus surprising and unexpected that two quaternary ammonium salts were found to have high, rapid-kill bactericidal activity in the presence of copper, with or without OXONE monopersulfate compound. These are: (1) (hydrogenated tallow) 2-ethylhexyl dimethyl ammonium chloride and (2) dicoco dimethyl ammonium chloride. Test results are summarized in Table 2 and clearly show that copper does not diminish the activity of these quaternary ammonium salts unlike the above systems, and that with copper present, greater than 99.9% of the bacteria is killed in one minute or less.

RESISTANT BACTERIA LABORATORY TESTING

A. Development of Resistant Bacteria

A standard 6,800 gallon, vinyl plastic lined swimming pool equipped with a standard diatomaceous earth filter was treated with 20 ppm of (hydrogenated tallow) 2-ethylhexyl dimethyl ammonium chloride, and the treated water allowed to circulate through the filter on a cycle time of 12 hours on and 12 hours off. The pool water contained an alkalinity of 100 ppm and a calcium hardness of 200 ppm and was maintained at a pH of 7-8 during the test. As needed, small amounts of the quaternary ammonium salt were added to maintain the quaternary ammonium salt at 15-20 ppm. The pool was "shocked" with 12 ppm OXONE monopersulfate compound weekly.

After 5 weeks, the count of bacteria resistant to the quaternary ammonium salt reached 970 cfu/ml. From the fifth test week to the end of the test (12 weeks), 330 ml of an algae suspension containing approximately 80 billion mixed bacteria was added weekly. By the seventh week of testing, bacteria counts of resistant bacteria reached greater than 3,000 cfu/ml in the swimming pool.

B. Preparation of Test Solutions

The copper ($Cu^{+2}$) solution used for testing against resistant bacteria was prepared as a 18% by weight copper sulfate pentahydrate solution in dechlorinated tapwater.

C. Bactericidal Efficacy Testing

For testing the effect of copper upon bacteria resistant to (hydrogenated tallow) 2-ethylhexyl dimethyl ammonium chloride, 10 ml of the above-described bacterial-contaminated pool water having about 1,000 cfu/ml of resistant bacteria was treated with the appropriate amounts of copper solution corresponding to 0.1 to 0.5 ppm $Cu^{+2}$. Using the appropriate procedure for sampling and neutralization, as described under "COMPARATIVE LABORATORY TESTING", colonies were counted at 1 through 5 minutes of contact. The results are shown in Table 3.

TABLE 3

| EFFECT OF COPPER ($Cu^{+2}$) ON RESISTANT BACTERIA | | | | | |
|---|---|---|---|---|---|
| $CU^{+2}$ (PPM) | Bacteria Remaining (cfu/ml) | | | | |
| | 1 Min. | 2 Min. | 3 Min. | 4 Min. | 5 Min. |
| 0.1 | 143 | 121 | 143 | 125 | 107 |
| 0.2 | 71 | 41 | 21 | 23 | 15 |
| 0.3 | 2 | 0 | 4 | 1 | 1 |
| 0.4 | 2 | 2 | 3 | 1 | 1 |
| 0.5 | 1 | 2 | 1 | 0 | 0 |

D. Conclusions

As shown in Table 3, the addition of copper to the resistant bacterial-contaminated pool water resulted in a rapid lowering of the bacteria count even at 0.1 ppm $Cu^{+2}$ with a 1-minute contact time.

LONG-TERM SWIMMING POOL TEST

A. Test Pools

Comparative tests were performed in two pools having a water capacity of 6,800 gallons. The pools were filled with water and the alkalinity adjusted to 100 ppm, and the calcium hardness adjusted to 200 ppm using standard swimming pool chemicals. The pH was adjusted to 7.5 initially and maintained at pH 7-8. Each swimming pool was equipped with a standard diatomaceous filter through which the pool water circulated for 12 hours per day.

B. Chemical Addition

To the above-described pools were added 12 ppm OXONE monopersulfate compound and 20 ppm (hydrogenated tallow) 2-ethylhexyl dimethyl ammonium chloride. To pool No. 1 was added 1 ppm Cu$^{+2}$ (as copper sulfate pentahydrate); pool No. 2 received no copper additions. The quaternary ammonium salt was maintained at 15-20 ppm; and the copper was maintained at 0.8-1 ppm. OXONE monopersulfate compound was added weekly at 12 ppm to both pools. C. Measurement of Bacteria Standard methods for ascertaining the bacteria counts were followed, as described above. The results are shown in Table 4.

TABLE 4

BACTERIA LEVELS IN SWIMMING POOLS

| Day (No.) | Bacteria Count (cfu/ml) | |
|---|---|---|
| | Pool 1 | Pool 2 |
| 0 | 0 | 0 |
| 7 | 0 | 0 |
| 14 | 0 | 0 |
| 21 | 0 | 0 |
| 28 | 0 | 0 |
| 35 | 0 | 0 |
| 40 | 0 | 720 |
| 42 | 0 | 0 |
| 49 | 0 | 0 |
| 54 | 0 | >3,000 |
| 56 | 0 | 0 |
| 63 | 0 | 0 |
| 70 | 0 | 63 |
| 75 | 23 | >3,000 |
| 77 | 0 | >3,000 |
| 82 | 83 | >3,000 |

D. Conclusions

Table 4 shows comparative data for pool No. 1 (containing 20 ppm (hydrogenated tallow) 2-ethylhexyl dimethyl ammonium chloride, 1 ppm copper (II) ion, and a weekly treatment of 12 ppm OXONE monopersulfate compound and pool No. 2 (same as for pool No. 1 except that no copper (II) ion was added). On day 35, 330 ml of an algae suspension containing about 80 billion mixed bacteria was added; this addition was repeated weekly. Thereafter, during the 12-week test, the highest bacteria count for pool No. 1 was 83 cfu/ml. For pool No. 2, the bacteria count exceeded 3,000 cfu/ml on numerous occasions. From the results it is seen that the presence of copper (II) ion with this particular quaternary ammonium salt gave bacteria control of the resistant bacteria in the swimming pool whereas the presence of this quaternary ammonium salt alone was not effective against this resistant bacteria.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A sanitizer composition comprising a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; and (b) a copper (II) ion source.

2. The sanitizer composition of claim 1 wherein said quaternary ammonium compound is (hydrogenated tallow) 2-ethylhexyl dimethyl ammonium chloride.

3. The sanitizer composition of claim 1 wherein said quaternary ammonium compound is (hydrogenated tallow) 2-ethylhexyl dimethyl ammonium methosulfate.

4. The sanitizer composition of claim 1 wherein said quaternary ammonium compound is dicoco dimethyl ammonium chloride.

5. The sanitizer composition of claim 1 wherein said copper (II) ion source is selected from the group consisting of copper (II) carbonate, copper (II) benzoate, copper (II) bicarbonate, copper (II) nitrate, copper (II) chloride, copper (II) sulfate, copper (II) bromide, copper (II) acetate, copper (II) formate, copper (II) trichloroacetate, copper (II) triethanolamine complex, copper (II) ethylenediamine tetraacetic acid complex, copper (II) citrate, copper (II) gluconate, and mixtures thereof.

6. The sanitizer composition of claim 1 wherein said copper (II) ion source is copper (II) sulfate.

7. The sanitizer composition of claim 1 wherein the weight ratio of said quaternary ammonium compound to said copper (II) ion source is from about 3:1 to about 600:1.

8. The sanitizer composition of claim 1 wherein said quaternary ammonium compound is selected from the group consisting of (hydrogenated tallow) 2-ethylhexyl dimethyl ammonium chloride, (hydrogenated tallow) 2-ethylhexyl dimethyl ammonium methosulfate and mixtures thereof and said copper (II) ion source is copper sulfate and the weight ratio of said quaternary ammonium compound to said copper (II) ion source is from about 10:1 to about 150:1.

9. The sanitizer composition of claim 8 wherein said weight ratio of said quaternary ammonium compound to said copper (II) source is from about 25:1 to about 75:1.

10. The sanitizer composition of claim 1 wherein said quaternary ammonium compound is dicoco dimethyl ammonium chloride and said copper (II) ion source is copper (II) sulfate and the weight ratio of said quaternary ammonium compound to said copper (II) ion source is from about 30:1 to about 300:1.

11. The sanitizer composition of claim 10 wherein said weight ratio of said quaternary ammonium compound to said copper (II) source is from about 60:1 to about 150:1.

12. A process for sanitizing water in a swimming pool, spa or hot tub, wherein the level of bacteria in said water is lowered comprising treating said water with a bactericidal effective amount of the combination of (a) a quaternary ammonium compound selected from the group consisting of a (hydrogenated tallow) 2-ethylhexyl dimethyl ammonium salt; a dicoco dimethyl ammonium salt, and mixtures thereof and (b) copper (II) ions, the concentration of said quaternary ammonium salt being less than about 60 ppm by weight.

13. The process of claim 12 wherein the concentration of said copper (II) ions is from about 0.1 to about 2 ppm by weight.

14. The process of claim 12 wherein the combination of (a) and (b) is sufficient to result in effective bactericidal activity in said water having a contact time not in excess of 60 seconds.

15. The process of claim 12 wherein said quaternary ammonium compound is (hydrogenated tallow) 2-ethylhexyl dimethyl ammonium chloride.

16. The process of claim 12 wherein said copper salt is copper sulfate.

17. The process of claim 12 additionally comprising contacting said body of water with a peroxy compound.

18. The process of claim 17 wherein said peroxy compound is hydrogen peroxide.

19. The process of claim 17 wherein said peroxy compound is potassium peroxymonosulfate.

20. The process of claim 12 wherein the concentration of said quaternary ammonium compound in said water is from about 5 to about 40 ppm by weight.

* * * * *